United States Patent [19]

Schmader

[11] 4,121,581
[45] Oct. 24, 1978

[54] PATIENT VENTILATOR MONITOR

[75] Inventor: Ronald G. Schmader, Hoffman Estates, Ill.

[73] Assignee: Sandoz, Inc., E. Hanover, N.J.

[21] Appl. No.: 737,212

[22] Filed: Nov. 1, 1976

[51] Int. Cl.² ............................................. A61M 16/00
[52] U.S. Cl. ........................... 128/145.8; 128/DIG. 29
[58] Field of Search ........................... 128/145.5–145.8, 128/142 R, 142.3, 147, 2.08, 188, DIG. 17, DIG. 29

[56] References Cited

U.S. PATENT DOCUMENTS

| | | | |
|---|---|---|---|
| 3,343,529 | 9/1967 | Miller et al. | 128/2.08 |
| 3,923,056 | 12/1975 | Bingmann et al. | 128/DIG. 17 X |
| 3,946,729 | 3/1976 | Hanna | 128/DIG. 29 X |
| 3,949,749 | 4/1976 | Stewart | 128/142.3 X |

FOREIGN PATENT DOCUMENTS 2,403,950   8/1974   Fed. Rep. of Germany ........ 128/145.8

Primary Examiner—Henry J. Recla
Attorney, Agent, or Firm—Gerald D. Sharkin; Robert S. Honor; Walter F. Jewell

[57] ABSTRACT

A ventilator monitoring system wherein the ventilator is in simultaneous fluid communication with a patient circuit and an exhaust circuit. The patient circuit comprises an inspiratory branch and an expiratory branch. A first one-way valve in the patient circuit inspiratory branch permits ingress only of a gas to the patient circuit. A second one-way valve in the patient circuit expiration branch permits egress only of patient exhaust gas to an expiration valve in the exhaust circuit. A monitor in the patient circuit expiration branch, monitors only the gas actually expired by the patient and not a combination of patient expired gas and excess gas from the ventilator.

11 Claims, 1 Drawing Figure

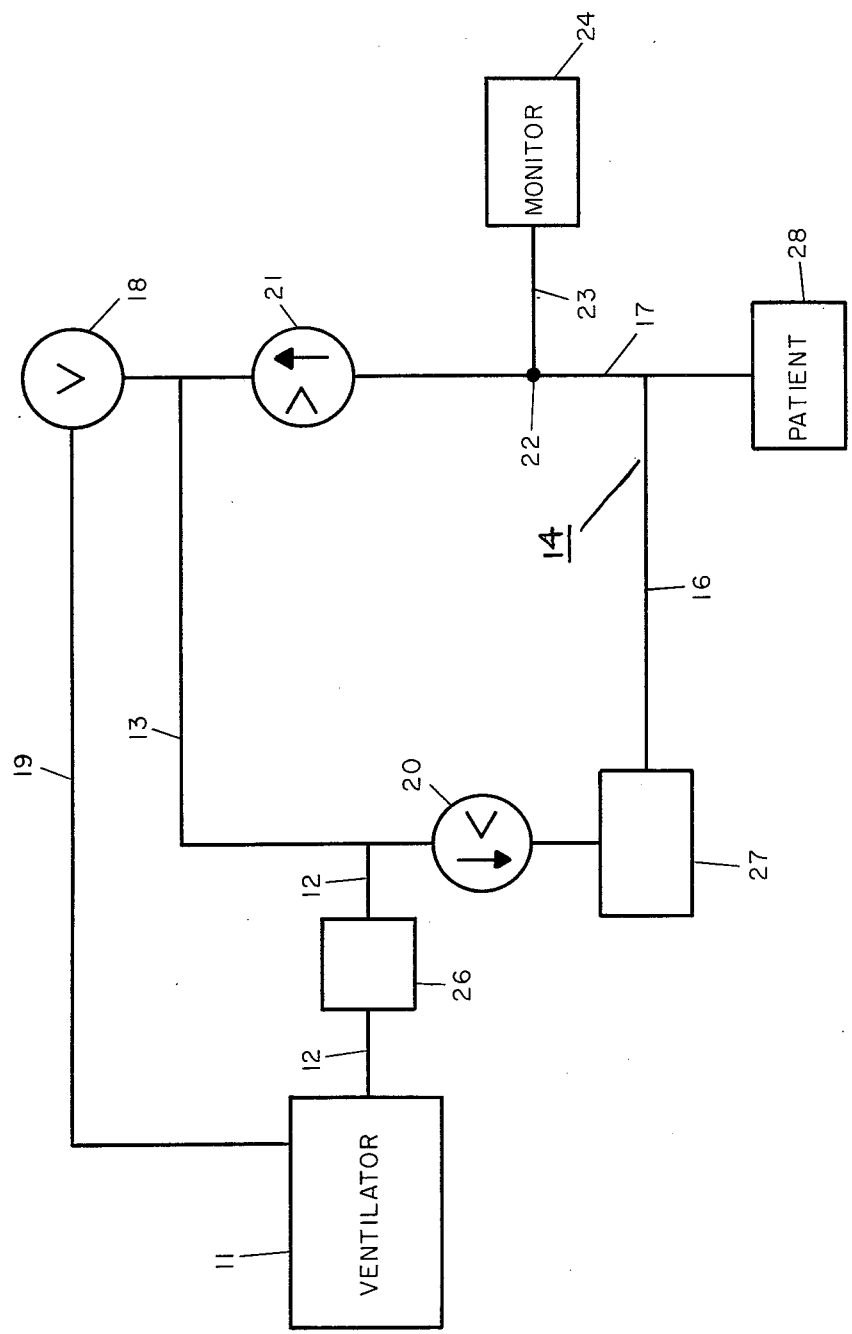

PATIENT VENTILATOR MONITOR

BACKGROUND OF THE INVENTION

This invention relates to monitoring systems. More particularly, it relates to ventilator monitoring systems.

Ventilators are used to provide supplemental or complete respiration to a patient who is unable to maintain sufficient respiration without assistance. These ventilators provide positive pressure to force gas, e.g., air, into the lungs of a patient to assist in inspiration. This is followed by expiration by the patient without assistance. This cycle is repeated at a predetermined rate.

It is important that the effectiveness of supplemental or complete respiration be effectively determined. One method of accomplishing this is by periodic blood gas measurements. However, it is not feasible to monitor blood gas continuously. Therefore, the effectiveness of supplemental or complete respiration is monitored by measuring the volume of gas used to ventilate the patent.

Prior art monitoring systems monitor the output port of the expiration valve of the ventilator system. However, in actual practice under some conditions (i.e., simv*) the patient may not be required to take all of the gas delivered by the ventilator. Any excess gas from the ventilator is shunted into the expiration valve where it exits along with the gas volume expired by the patient. Thus, the expiration valve monitor may not monitor the true volume of gas expired by the patient but actually a combination of patient gas and excess gas from the ventilator.

*synchronized intermittent mandatory ventilation.

It is therefore an object of this invention to provide an apparatus and method for monitoring only the gas volume actually expired by the patient in a ventilation system.

SUMMARY OF THE INVENTION

Broadly, this invention provides a ventilator monitoring system comprising a ventilator in simultaneous fluid communication with a patient circuit, and an exhaust circuit having an expiration valve. The patient circuit comprises an inspiratory branch and an expiratory branch. A first valve means is provided in the patient circuit inspiration branch for permitting ingress only of a gas from the ventilator to the circuit.

A second valve means is provided in the patient circuit expiration branch which is in fluid communication with the exhaust circuit and the expiration valve. The valve means permitting egress only of a patient exhaust gas to the expiration valve.

The first and second valve means each comprise a one-way valve.

Monitoring means comprising a gas flow monitor are provided upstream of the second valve means in fluid communication with the patient circuit expiration branch for monitoring the gas volume expired by the patient.

It is a feature of this invention that the gas flow monitor of the monitoring means comprise a flow transducer.

Additionally, the ventilator gas may be filtered and humidified prior to delivery to the patient.

In operation, the gas volume expired by a patient through the expiration valve of a patient ventilator system may be monitored by;

(a) supplying a gas flow from a ventilator to a patient gas circuit while simultaneously shunting any excess gas to an exhaust gas circuit;

(b) preventing back flow of the gas from the patient circuit to the exhaust circuit upon patient expiration; and (c) monitoring the patient expired gas prior to exhausting the gas through an expiration valve in the exhaust gas circuit, while simultaneously preventing any excess gas from entering the patient circuit.

It is a preferred embodiment of this invention that the gas in the patient circuit is prevented from back-flowing into the exhaust circuit by passing the gas through a one-way valve in the patient gas circuit.

It is an additional preferred embodiment of this invention that after monitoring the patient expired gas, that the gas is passed through a one-way valve, which simultaneously emits the expired gas to the expiration valve and prevents the exhaust gas from entering the patient circuit.

BRIEF DESCRIPTION OF THE DRAWING

The single FIGURE is a block diagram illustrating the ventilation patient monitor interconnections of the patient monitor of this invention.

DETAILED DESCRIPTION OF AN EMBODIMENT OF THE INVENTION

This invention will best be understood by the following detailed description:

Referring now to the FIGURE there is shown a ventilator 11 in fluid communication via conduit 12 with an exhaust circuit 13 and a patient circuit shown generally at 14. The patient circuit 14 comprises an inspiratory branch 16 and an expiratory branch 17.

An expiration valve 18 is in fluid communication with the exhaust circuit 13 and the expiratory branch 17 of the patient circuit 14, and is controlled by an expiration valve control line 19.

A one-way valve 20 is situated in the inspiratory branch 16 of the patient circuit 14, which valve permits gas flow from the ventilator 11 to enter the inspiratory branch 16, but prevents back flow of patient gas into the exhaust circuit 13.

A second one-way valve 21 is situated in the expiratory branch 17 of the patient circuit 14, downstream of the gas flow monitor 22. The valve 21 is in fluid communication with both the expiratory branch 17, of the patient circuit 14, and the exhaust circuit 13. The valve 21 permits gas flow from the expiratory branch 17 to the expiration valve 18, but prevents exhaust gas in the exhaust circuit 13 from entering the expiratory branch 17.

The gas flow monitor 22, e.g., a flow transducer, is in electrical communication via conduit 23 with a conventional monitor 24, e.g., a Monaghan 700* ventilator monitor.

* Monaghan a Division of Sandoz, Inc.

Also shown are a filter 26, e.g., a bacteria filter, and a humidifier 27, whereby the ventilator gas is filtered and humidified prior to delivery to the patient. While the filter 26 and humidifier 27 are preferred they are not necessary to operation of the apparatus of this invention.

In operation during a voluntary patient inspiration cycle the expiration valve control line 19 is not activated by the ventilator 11 maintaining the expiration valve 18 open. The amount of gas, e.g., oxygen, pumped from the ventilator 11 to the patient 28 via conduits 12, one-way valve 20 and the inspiratory branch 16 of the patient circuit 14 is determined by the patient's own effort to breath.

Any excess ventilator gas not desired by the patient 28 is shunted to the expiration valve 18 via the exhaust circuit 13.

After delivery of the predetermined volume of the gas, the ventilator ceases.

During the inhalation phase, there is greater pressure in the exhaust circuit 13 with the one-way valve 21 being held closed preventing back flow of excess gas into the patient circuit 14.

Upon patient 28 expiration, the pressure on one-way valve 21 is greater in the expiratory branch 17 of the patient circuit 14, opening the valve 18 and permitting patient expiratory gas flow past the gas flow monitor 22 through the one-way valve 21 and then through the expiration valve 18. One-way valve 20 is closed due to pressure in the patient circuit 14, preventing any back flow of patient expired gas through the valve 20.

When the patient is not breathing, the pressure is greater in the exhaust circuit 13, closing the one-way valve 21 and thus preventing any gas flow into the patient circuit 14.

During a mandatory breath, the ventilator 11 activates the expiration valve 18 so that the entire predetermined volume is delivered to the patient 28. Expiration proceeds as described above.

This invention provides for superior patient ventilation monitoring over that of the prior art in that the volume of gas expired by the patient is monitored. In the prior system, the total delivered volume of gas from a ventilator was sensed by the flow transducer and hence it was not known what portion of the delivered gas was actually expired by a patient.

What is claimed is:

1. A ventilator monitoring system comprising a patient cirucit, an exhaust circuit and ventilator means adapted for an inhalation cycle, an exhalation cycle and for an intermittent mandatory ventilation cycle, said ventilator means being in simultaneous fluid communication with patient circuit and said exhaust circuit having an expiration valve;

the patient circuit comprising in fluid communication an inspiratory branch and an expiratory branch;
    a first valve means in the patient circuit inspiratory branch in fluid communication with the exhaust circuit for permitting ingress only of a gas from the ventilator to the patient circuit;
    a second valve means in the patient circuit expiratory branch in fluid communication with the exhaust circuit and the expiration valve; the second valve means permitting egress only of a patient exhaust gas to the expiration valve;
    said ventilator means maintaining said expiratory valve closed only during an intermittent mandatory ventilation cycle; and
    monitoring means comprising a gas flow monitor upstream of the second valve means in fluid communication with the patient circuit expiratory branch for monitoring the gas volume expired by the patient.

2. The ventilator monitoring system of claim 1 wherein the first and second valve means each comprise a one-way valve.

3. The ventilator monitoring system of claim 2 wherein the monitoring means of the gas flow monitor is a flow transducer.

4. The ventilator monitoring system of claim 3 wherein a filter means is in fluid communication with the ventilator, the patient circuit and the exhaust circuit.

5. The ventilator monitoring system of claim 4 wherein a humidifier is in fluid communication with the patient circuit inspiration branch.

6. A method of measuring the gas volume expired by a patient through the expiration valve of patient ventilator system comprising the steps of:
    (a) supplying a gas flow from a ventilator to a patient gas circuit while simultaneously shunting any excess gas to an exhaust gas circuit;
    (b) preventing back flow of the gas from the patient circuit to the exhaust circuit upon patient expiration,
    (c) exhausting patient expired gas to the exhaust circuit; and
    (d) monitoring the patient expired gas prior to exhausting the gas through an expiration valve in the exhaust gas circuit, while simultaneously preventing any excess gas from entering the patient circuit.

7. The method according to claim 6 wherein the gas in the patient circuit is prevented from back flowing into the exhaust circuit by passing the gas through a one-way valve in the patient gas circuit.

8. The method according to claim 7 wherein after monitoring the patient expired gas, the gas is passed through a one-way valve, which simultaneously emits the expired gas to the expiration valve and prevents the exhaust gas from entering the patient circuit.

9. The method according to claim 8 wherein the gas from the ventilator is first passed through a filter before being supplied to the patient.

10. The method according to claim 9 wherein the patient gas is humidified prior to delivery to the patient.

11. A gas delivery-monitoring system for ventilator means having an inhalation cycle, an exhalation cycle and an intermittent mandatory ventilation cycle comprising a patient circuit and exhaust circuit having an expiration valve means, said patient circuit being in fluid communication with said exhalation circuit; said ventilator means maintaining said expiration valve means closed only during an intermittent mandatory ventilation cycle;
    the patient circuit comprising in fluid communication an inspiratory branch and an expiratory branch;
    a first valve means in the patient circuit inspiratory branch in fluid communication with the exhaust circuit for permitting ingress only of a gas from a ventilator to the patient circuit;
    a second valve means in the patient circuit expiratory branch in fluid communication with the exhaust circuit and the expiration valve; the second valve means permitting egress only of a patient exhaust gas to the expiration valve; and
    means upstream of the second valve means in fluid communication with the patient circuit expiratory branch for engaging monitoring means for monitoring the gas volume expired by a patient.

* * * * *